(12) United States Patent
Bruno

(10) Patent No.: US 9,746,399 B2
(45) Date of Patent: Aug. 29, 2017

(54) HEADSPACE SAMPLING DEVICE AND METHOD FOR SAMPLING

(71) Applicant: National Institute of Standards and Technology, Gaithersburg, MD (US)

(72) Inventor: Thomas J. Bruno, Broomfield, CO (US)

(73) Assignee: The Unites States of America as represented by the Secretary of Commerce, The National Institute of Standards and Technology, Washington, DC (US)

( * ) Notice: Subject to any disclaimer, the term of this patent is extended or adjusted under 35 U.S.C. 154(b) by 358 days.

(21) Appl. No.: 13/974,181

(22) Filed: Aug. 23, 2013

(65) Prior Publication Data

US 2014/0057361 A1   Feb. 27, 2014

Related U.S. Application Data

(60) Provisional application No. 61/692,777, filed on Aug. 24, 2012.

(51) Int. Cl.
  *G01N 1/44*   (2006.01)
  *G01N 1/40*   (2006.01)
  *G01N 31/12*  (2006.01)
  *G01N 1/22*   (2006.01)
  *G01N 30/06*  (2006.01)

(52) U.S. Cl.
  CPC ............. *G01N 1/44* (2013.01); *G01N 1/4022* (2013.01); *G01N 31/12* (2013.01); *G01N 2001/2229* (2013.01); *G01N 2030/062* (2013.01)

(58) Field of Classification Search
  CPC  G01N 31/12; G01N 1/22; G01N 1/44; G01N 7/04; G01N 27/12; G01N 2030/025; G01N 30/30
  See application file for complete search history.

(56) References Cited

U.S. PATENT DOCUMENTS

| | | | | |
|---|---|---|---|---|
| 3,057,692 | A | * 10/1962 | Van Kirk | B01D 7/00 422/78 |
| 3,684,454 | A | * 8/1972 | Martin et al. | G01N 27/16 219/499 |
| 5,363,707 | A | 11/1994 | Augenblick et al. | |
| 5,866,072 | A | 2/1999 | Bowe, Jr. et al. | |
| 6,146,895 | A | 11/2000 | Green et al. | |
| 6,286,375 | B1 | 9/2001 | Ward | |

(Continued)

OTHER PUBLICATIONS

Simple Quantitative Headspace Analysis by Cryoadsorption on a Short Alumina Plot Column Thomas J. Bruno Journal of Chromatographic Science, vol. 47, Aug. 2009.*

*Primary Examiner* — Lyle Alexander
*Assistant Examiner* — Dwan A Gerido
(74) *Attorney, Agent, or Firm* — Steve Witters; Witters and Associates

(57) ABSTRACT

A device and method for headspace sampling is disclosed herein. The headspace sampling device comprises a sample holding device configured to be sealed in a vial. The sample holding device has a pair of electrodes gap spaced from one another and a basket extending between the electrodes configured to hold a sample. The basket is configured to heat a sample held therewith and volatize at least a portion of the sample upon an electrical current being passed through the electrodes and the basket.

16 Claims, 8 Drawing Sheets

(56) References Cited

U.S. PATENT DOCUMENTS

| | | |
|---|---|---|
| 6,395,560 B1 | 5/2002 | Markelov |
| 6,436,710 B1 | 8/2002 | Sivavec et al. |
| 6,960,477 B2 | 11/2005 | Tanimoto et al. |
| 7,082,849 B2 | 8/2006 | Chida et al. |
| 7,409,880 B2 | 8/2008 | Hale et al. |
| 7,484,399 B2 | 2/2009 | Wohltjen et al. |
| 7,709,267 B2 | 5/2010 | Tipler et al. |
| 8,062,905 B1 | 11/2011 | Meece et al. |
| 8,075,842 B1 | 12/2011 | Meece et al. |
| 8,247,239 B2 | 8/2012 | Tipler et al. |
| 8,425,633 B2 | 4/2013 | Banasiak et al. |
| 2013/0078735 A1 | 3/2013 | Sandra et al. |
| 2013/0151167 A1 | 6/2013 | Broughton |

\* cited by examiner

HEADSPACE SAMPLING DEVICE AND METHOD FOR SAMPLING

CROSS-REFERENCE TO RELATED APPLICATIONS

This application claims the benefit of U.S. Provisional Application No. 61/692,777, filed Aug. 24, 2012.

STATEMENT REGARDING FEDERALLY SPONSORED RESEARCH OR DEVELOPMENT

This work is funded by the National Institute of Standards and Technology under the U.S. Department of Commerce.

FIELD OF THE INVENTION

This invention relates to a device and method for sampling, and more particularly to a headspace sampling device and method for making and using the headspace sampling device.

BACKGROUND

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

Headspace sampling devices and systems typically comprise a vial configured to receive and hold a sample and for the introduction of a sparging or inert gas through the vial. The gas carries headspace vapor from the vial to an analytical device. Typical sampling devices may have a vial sealed with a diaphragm or septum. They are typically configured to have a probe pierce the septum to provide a flow of sparging gas from the sample headspace of the vial to the entrance of an analytical instrument, for analysis of the headspace.

Headspace analysis is a technique in which a gas that has previously been in contact with a sample in a condensed phase (solid, liquid, or semi-solid) is examined for the presence of volatile compounds released into the gas. The partitioning of analytes into the gas phase may be understood or even predicted with thermodynamic considerations. This thermodynamic relationship may sometimes make possible the approximation of analyte concentration in the original condensed phase. Headspace analysis may typically be easily accomplished for volatile analytes in a nonpolar matrix. Other sample presentations may be more difficult with known headspace sampling devices.

Sampling methods from headspaces may be either static or dynamic. In static methods, one typically pressurizes a sealed vial or vessel containing the condensed analyte (to slightly above atmospheric pressure), then sampling may be done of the pressurized headspace through a septum. Sampling may be done with a gas tight syringe (with or without a syringe valve), a multiport sampling valve, or with a solid phase microextraction (SPME) fiber. In dynamic methods, a flow of carrier or sweep gas may be applied to the matrix containing the analyte. The stream may then be collected in a cryostat, adsorbent or solvent, thus this method is often referred to as purge and trap. The sweep gas may be under a positive pressure or drawn through the sample at reduced pressure.

When the analyte in the headspace gas is at a trace level, or when an exhaustive analysis of all constituents is desired, purge and trap methods are often preferred over static headspace or even modern SPME approaches. For analytes of very low volatility, longer collection times are required to collect sufficient sample for analysis. One means of obtaining a sample and introducing it into an analytical instrument, such as a chromatographic column, is known as "headspace sampling". In conventional headspace sampling, sample material is sealed in a vial and subjected to constant temperature conditions for a specified time. Analyte concentrations in the vial gas phase should reach equilibrium with the liquid and/or solid phases during this thermostatting time. The vial is subsequently pressurized with carrier gas to a level greater than the "natural" internal pressure resulting from thermostatting and equilibration. Then the pressurized vial is connected to the chromatographic column in such a way as to allow for the transfer of a portion of the vial gas phase into the column for a short period of time.

A technique for delivering sample vapor to an analytical instrument is a 'purge and trap' apparatus. A purge and trap apparatus is used for capturing and identifying volatile organic compounds in a sample. Purge and trap system are configured for sparging liquid or solid samples containing volatile organic compounds at a controlled temperature with a regulated flow of inert gas for a fixed period of time. Sparging gas enters through a needle adaptor and passes through a sparging needle which is inserted into a vial containing a sample therein.

Gas chromatography is one of the most common analytical instruments used for the separation of compounds for the purpose of purification, identification, and quantification. The sparging gas passes through the sample and strips analytes from the sample which are accumulated and concentrated on a cool sorbent trap. The sorbent trap comprises a stationary phase or material suitable to collect the material to be accumulated for analysis. The trap functions as a sample concentrator which thermally traps and selectively later desorbs organic compounds for analysis.

After the material of interest is accumulated in the trap, the trap is then rapidly heated. The analytes are then desorbed from the trap as a plug and are moved by a flow of carrier gas which passes into the gas chromatograph. The gas chromatograph provides an output indicative of the substances in the sample. The sample is swept through the column by an inert carrier gas. After passing through the column, the separated solutes flow through a detector the output of which is displayed on a recorder or computer.

SUMMARY

In at least one aspect of the present disclosure, a headspace sampling device is provided. The headspace sampling device comprises a vial and a sample holding device. The sample holding device comprises a first electrode, a second electrode gap spaced from the first electrode, and a basket configured to hold a sample and having a portion extending between the first electrode and the second electrode, spanning the gap space therebetween. The basket is configured to heat a sample held therewith and volatize at least a portion of the sample upon an electrical current being passed through the first electrode, the basket, and the second electrode. The sample holding device is configured to seal the basket in the vial.

In at least one other aspect of the present disclosure, a headspace sampling device comprises a sample basket sealed in a sample container. The sample basket is configured and disposed to hold a liquid, semi-solid, or solid sample. A pair of electrodes extend into the sealed container and are configured and disposed to form and hold the sample basket. The sample basket is configured to heat a sample held therewith upon an electrical current being passed through the pair of electrodes.

In at least one additional aspect of the present disclosure, a method of headspace sampling is provided, the method comprises the steps of: placing a solid, semi-solid, or liquid sample on a sample basket and holding the sample therewith; sealing the sample basket holding the sample in a container or vial; electrically heating the basket and volitizing at least a portion of the sample; and analyzing the volitized portion of the sample.

BRIEF DESCRIPTIONS OF THE DRAWINGS

The following Figures, which are idealized, are not to scale and are intended to be merely illustrative and non-limiting.

DETAILED DESCRIPTION

Figure 1:
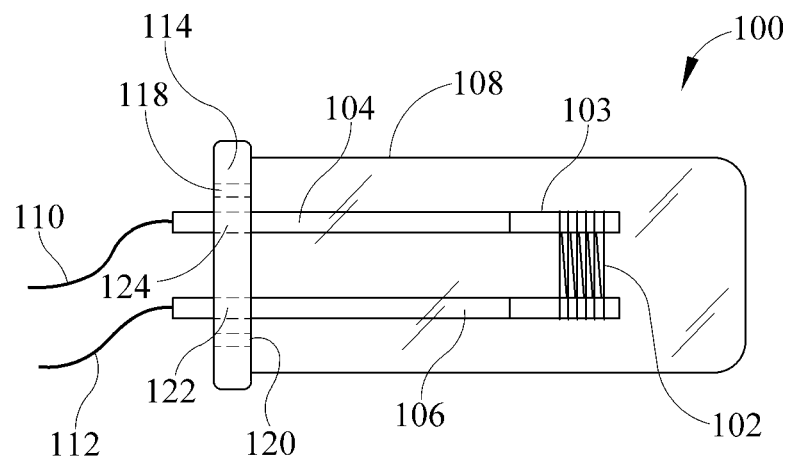
FIG. 1 is a schematic representation of a top view of a headspace sampling device of the present disclosure.

A detailed description will now be provided. Each of the appended claims is to be recognized as including equivalents to the various elements or limitations specified in the claims. Depending on the context, all references below to the "invention" or disclosure may in some cases refer to certain specific aspects only. In other cases it will be recognized that references to the "invention" will refer to subject matter recited in one or more, but not necessarily all, of the claims. Each of the inventions is described in greater detail below, including specific aspects, versions and examples, but the disclosure is not limited to these aspects, versions or examples, which are included to enable a person having ordinary skill in the art to make and use the inventions when the information in this patent is combined with available information and technology.

Various terms as used herein. To the extent a term used in a claim is not defined herein, it should be given the broadest definition persons in the pertinent art have given that term as reflected in printed publications and issued patents at the time of filing. Additionally, unless otherwise specified, all compounds or examples described herein may be substituted or unsubstituted and the listing of compounds or examples includes derivatives thereof. Further, various ranges and/or numerical limitations may be expressly stated below. It should be recognized that unless stated otherwise, it is intended that endpoints are to be interchangeable and any ranges shall include iterative ranges falling within the expressly stated ranges or limitations.

An aspect of the present disclosure comprises a sampling device configured to make its own headspace. The sampling device may comprise a vial and a heater disposed in the vial. The heater may be configured and disposed to directly contact and hold a sample placed in the vial and make a headspace for collection and/or analysis upon heating. The heater may be configured to heat the sample by a sufficient amount to volatilize and/or pyrolyze at least one constituent in the sample. In at least one aspect, the heater is configured to pyrolyze the sample wherein the sample is thermally decomposed or thermally stressed to make the headspace. In at least one other aspect, the pyrolyzed heater settles to the bottom of the vial.

Aspects of the presently disclosed sampling device comprise a vial and a heater disposed in the vial. The heater may be configured to heat and/or pyrolyze a sample to produce sample vapor and/or products of pyrolyzation. The heater of the present disclosure may comprise a pair of electrodes having a wire winding around the pair of electrodes. The wire winding may form a basket configured to hold the sample in the vial. The sampling device may be a component part of a headspace vapor generation and collection device.

In at least one aspect of the present disclosed, a headspace sampling device of the present disclosure may be a component part of a system comprising a pyrolysis-gas chromatography-mass spectrometry. Pyrolysis-gas chromatography-mass spectrometry may provide a method of chemical analysis in which the sample is heated to decomposition to produce smaller molecules that are separated by gas chromatography and detected using mass spectrometry. Pyrolysis, as used herein, is the thermal decomposition of materials in an inert gas or vacuum. The sample may be heated to about 600-1000° C., or even higher temperatures, depending on the application. Large molecules in the samples cleave at their weakest points and produce smaller, more volatile fragments. These fragments may then be separated by gas chromatography. A Pyrolysis gas chromatograph (GC) chromatogram of the present disclosure may provide for a wide range of different decomposition products to be formed and analyzed. The data generated with aspects of the present disclosure may be used as fingerprint to prove material identity or the GC/mass spectrometry (MS), GC/MS, data may be used to identify individual fragments to obtain structural information.

The headspace sampling device of the present disclosure may be a component part of a system comprising an infrared spectroscopy or chromatography. It may be desirable to automatically submit a large number of samples or specimens to the analytical instrument performing the analysis without constant attendance. A number of types of automatic sampling systems (referred to generally as "autosamplers") are known and have embodiments for both solids and liquids, which may be configured to incorporate the headspace sampling device of the present disclosure.

The headspace sampling device of the present disclosure may be used to feed a field-portable gas chromatograph/mass spectrometers (GC/MS) which may be engineered specifically for on-site VOC analysis. These self-contained devices typically comprise a vacuum system, analytical components and power components within one compact unit and are capable of acquiring and analyzing VOC samples in the field.

The headspace sampling device of the present disclosure may be a component part of a Porous layer open tubular column-Cryoadsorption headspace sampling and analysis system. This system may provide dynamic headspace vapor collection on short, porous layer open tubular (PLOT) capillary columns maintained at low temperature. The headspace sampling device of the present disclosure may provide a small in situ pyrolysis platform that provides for rapid heating and rapid vapor capture for a wide variety of samples. This approach or system may be referred to as pyro-PLOT-cryo. For example, a PLOT column may be configured and disposed to collect headspace vapor generated with the presently disclosed headspace sampling device. The PLOT column may disposed in a cryostat and the headspace vapor generation and collection device may be configured for Pyrolysis PLOT-Cryoadsorption. PLOT-Cryoadsorption, or PLOT-Cryo analysis may be sensitive to 1 ppb (mass/mass), and may provide results that are of low enough uncertainty to permit thermodynamic interpretation through the van't Hoff equation.

Figure 2:
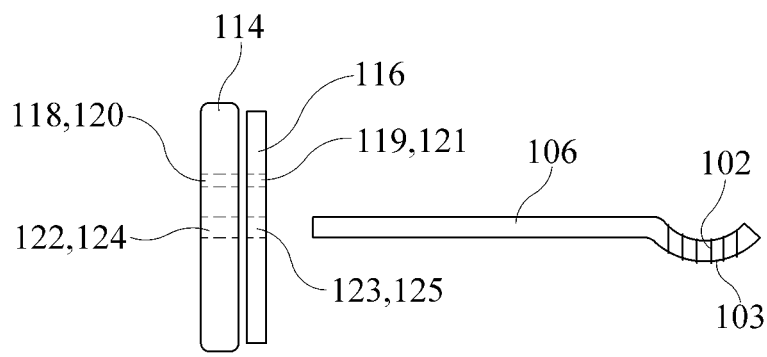
FIG. 2 is an exploded side view of a portion of the headspace sampling device of FIG. 1.

With reference to the Figures, aspects of the presently disclosed headspace sampling device will now be described. FIGS. 1 and 2 show headspace sampling device 100 comprising vial 108 with a sample holding device disposed therein. The sample holding device comprises a first electrode 104 and a second electrode 106. First and second electrodes 104 and 106 extend substantially parallel with one another into vial 100 and are gap spaced from one another. A basket 103 is configured to hold a sample and has a portion extending between first electrode 104 and second electrode 106, spanning the gap space therebetween. Basket 103 is configured to heat a sample held therewith and volatize at least a portion of the sample upon an electrical current being passed through first electrode 104, basket 103, and second electrode 106.

Headspace sampling device 100 may comprise a closure 114 and a septum 116. Closure 114 may be a screw type closure, or other type closure as known in the art, configured to close an open end of vial 108 and create a seal between septum 116 and vial 108. Closure 114 may have apertures 122 and 124 configured and disposed for the extension of first and second electrodes 104 and 106 therethrough. Closure 114 may also have apertures 118 and 120 configured and disposed for adapting a gas inlet and a gas outlet. Septum 116 may be configured to be pierced at locations 123 and 125 for the extension of first and second electrodes 104 and 106 therethrough. Alternatively, septum 116 may have apertures at locations 123 and 125 configured and disposed to align with apertures 122 and 124 in closure 114. Septum 116 may be configured to be pierced at locations 119 and 121 for the extension of a gas inlet and a gas outlet into vial 108. Alternatively, septum 116 may have apertures at locations 119 and 121 configured and disposed to align with apertures 118 and 120 and provide for a gas inlet and a gas outlet.

Basket 103 may comprise at least one of stainless steel, nickel-chromium, and tungsten extending between electrodes 104 and 106. Basket 103 may also comprise platinum or other material(s) and alloys that provide desired heating and/or pyrolyzing. For example, basket 103 may comprise at least one of stainless steel, nickel-chromium containing alloys, tungsten, tungsten alloys, platinum, platinum alloys, and other chemically stable materials with a high electrical resistance. Chemically stable materials, as used herein, means materials that are nonreactive in an ambient environment and upon contact with a sample. High electrical resistance, as used herein, means having a resistance to the flow of electricity to provide desired heating and/or pyrolyzing of the sample. In at least one aspect of the present disclosure, basket 103 comprises wire 102 wrapped around electrodes 104 and 106. Wire 102 may have at least one, or a sole, continuous strand wrapped around first electrode 104 and second electrode 106, spanning the gap space therebetween. Wire 102 may be configured to pyrolyze into a powder upon an electrical current being passed through first electrode 104, basket 113, and second electrode 106. Wire 102 may be configured to pyrolyze into a solid and have minimal, negligible, or no products of pyrolization exit vial 108.

In at least one aspect of the presently disclosed head space sampling device, electrodes 104 and 106 are made from two small copper lead wires that hold basket 103 comprising small diameter, high resistance stainless steel or NiCr wire 102. Wire 102 may have a diameter between about 0.0005 inch and 0.0025 inch. Basket 113 may be formed to accept a small sample, the mass of which may be in a range from 0.2 to 0.05 mg. Pyrolysis may be performed by use of a resistor capacitor circuit of the type used in spot welders to send an electrical current through first electrode 104, basket 113, and second electrode 106.

Figure 3:
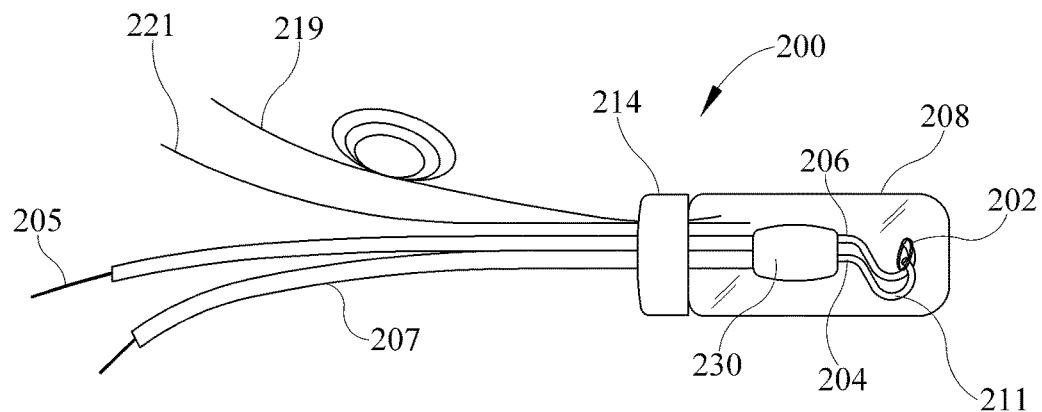
FIG. 3 is a perspective representation of a headspace sampling device of the present disclosure.
Figure 4:
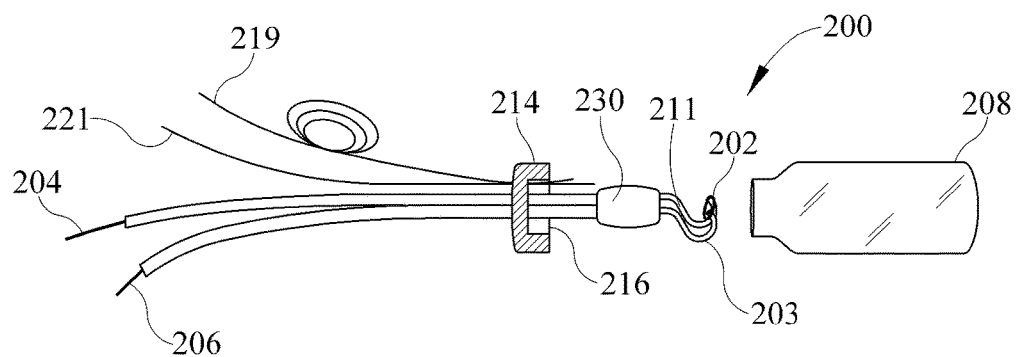
FIG. 4 is a partially exploded and cross-sectional representation of the headspace sampling device of FIG. 3.
Figure 5:
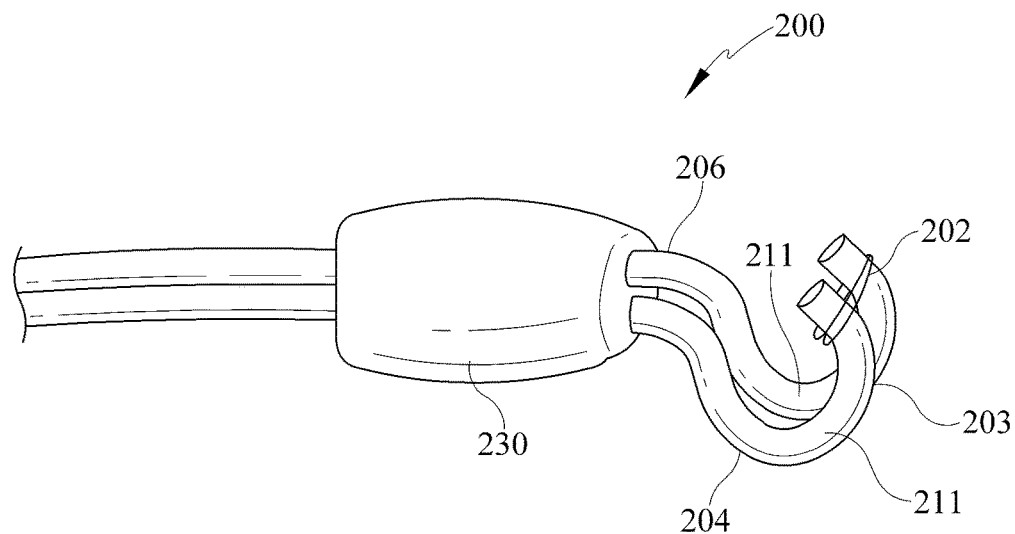
FIG. 5 shows the sample basket of the headspace sampling device of FIG. 3.

FIGS. 3-5 show headspace sampling device 200 comprising vial 208 with a sample holding device disposed therein. In at least one aspect of head space sampling device 200, electrodes 204 and 206 are made from two lengths of 22 gauge single strand tinned copper wire, approximately 5 cm in length. Electrodes 204 and 206 extend through closure 214 and septum 216 and into vial 208. At one end 205, of electrodes 204 and 206 outside of vial 208, the insulation 207, for example Teflon insulation, is stripped for a length of approximately 1 mm to provide a connection to a capacitor circuit. At the other end inside of vial 208, the insulation is stripped for approximately 3 mm, and two hooks 211 are formed approximating a half-circle or hook, shaping a basket 203. Proximate basket 203, a fixture 230 may be made by applying a bolus of ceramic cement, formulated for electrical resistance, thinned with sodium silicate solution. Bolus 230 may form a strong fixture upon curing and hold electrodes 204 and 206 in a gap spaced orientation inside vial 208. Gas inlet 221 and gas outlet 219 may extend through closure 214 and septum 216 and into vial 208.

Headspace sampling device 200 may be configured to be a component part of a Pyro PLOT-Cryo system. In at least one aspect of the present disclosure, septum 214 is configured to be pierced with electrodes 204 and 206 and connect to a capacitor firing circuit. For example, electrodes 204 and 206 may be configured to serve as connection wires of a typical automatic sampler vial (of the screw cap type) and configured to pierce septum 216. Septum 216 may comprise a silicone PTFE sandwich, with the silicone side facing hooks 211. A screw type closure 214 may then be placed onto septum 216 by forcing septum 216 into the inside of closure 214. A screw type closure 214 may be advantageous because the usual crimping tool used with crimp caps may not fit with the lead wires in place. However, the presently disclosed headspace sampling device is not limited to screw type closures as any closure configured to seal septum 216 with vial 208 may be used. In at least one aspect, a dental ball burnisher may be used to insert septum 206 into closure 214.

Sample basket 203 may be formed by winding about 15 loops of a high resistance wire 202 (for example, stainless steel, nickel-chromium, or tungsten wire) of small diameter (for example, a diameter of about 0.002 to 0.001 inch). The exact size and composition of the wire 202 is not critical and shall not be limited to the above examples. Any wire 202 configured to provide high electrical resistance and good chemical stability may be used. Wire 202 may be wound around hooks 211 by first placing a series of small scratches on the inside periphery of hooks 211. For example, a sharp scalpel may be used to create very small groves to guide and restrain wire 202. The surfaces of hooks 211 having the groves formed therein, may be wire brushed, for example a medium speed rotary tool such as a dental engine may be used to brush the hooks 211. Brushing hooks 211 may improve electrical contact between wire 202 and electrodes 204 and 206 by removing any accumulated oxide. The winding of the loops of wire 202 may be facilitated by a bobbin threader, fabricated from a spool of wire 202, and a small pin vise containing a ceramic tube with an internal diameter of about 0.5 mm. After the loops of wire 202 are placed around hooks 211, wire 202 may be cut and a pigtail tied to secure the loops of wire 202. The resulting basket 203 may be oval-shaped as shown in FIGS. 3-5.

Headspace sampling device 200 may be used by loading a sample into an oval shaped cylindrical basket 203, which may comprise about 15 loops of wire 202. The sample loaded into basket 203 may be solid, semi-solid, or liquid. For example a sample may be soft solid (such as a plastic explosive), a crystalline solid, a melt, a solution, or a dust. Samples may be loaded into basket 203 with instruments such as dental string packers or dental amalgam carriers. Alternatively, a user may simply drag or dip basket 203 through or into the sample. Sample masses may range from about 0.01 to about 1.5 mg, from about 0.06 to about 0.7 mg, or be about 0.2 mg. Vial 208 may then be screwed into closure 214 and gas inlet 221 and gas outlet 219 may be inserted into vial 208. For example, a PLOT capillary may be installed, along with a helium line. This may be performed with the PLOT capillary already in place inside a cryostat with one end leading to vial 208. In at least one aspect of the present disclosure, outlet 219 comprises a coiled PLOT column and may serve a dual role of transfer line and collection device.

Figure 6:
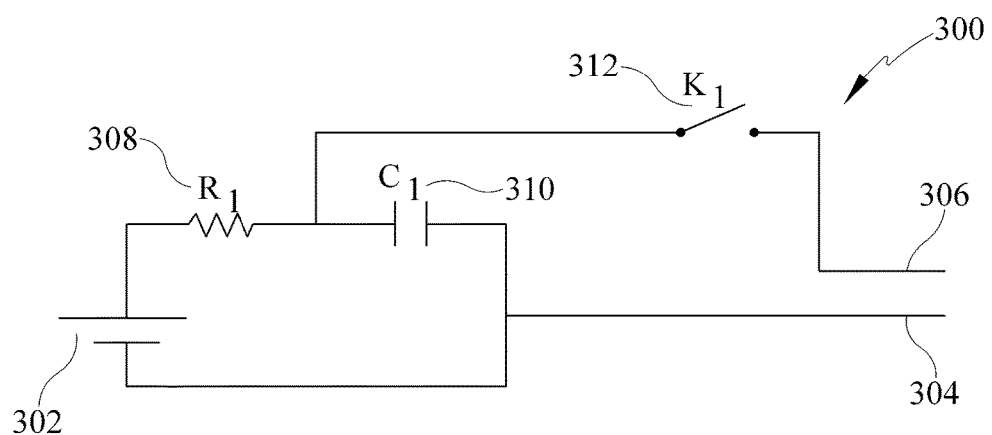
FIG. 6 shows a firing circuit configured to energize the headspace sampling device of the present disclosure.

FIG. 6 shows firing or energizing circuit 300 which may be used to energize headspace sampling device 100 or 200. Firing circuit 300 may be a capacitor firing circuit and have lead 304 configured and disposed to connect to an electrode 204 and lead 306 configured and disposed to connect to an electrode 206. Firing circuit 300 may be a simple circuit and may be configured similarly to a firing circuit that may be used to power a spot welder, for example. A regulated power supply 302 may be configured to apply 0.2 A at 18 V to charge capacitors 310. A single capacitor 310 is shown in FIG. 6 but may be representative of a plurality of capacitors connected in parallel. Capacitor 310 may have total capacitance of between about 40,000 µF and about 2,000,000 µF. Resistor 308 may have a resistance of about 100Ω. However, it is configured to protect the power supply and may have a resistance substantially higher or lower than 100Ω. Switch 312 is configured and disposed to complete the circuit between capacitor 310 and electrodes 204 and 206 and heat or pyrolyze basket 203.

Figure 7:
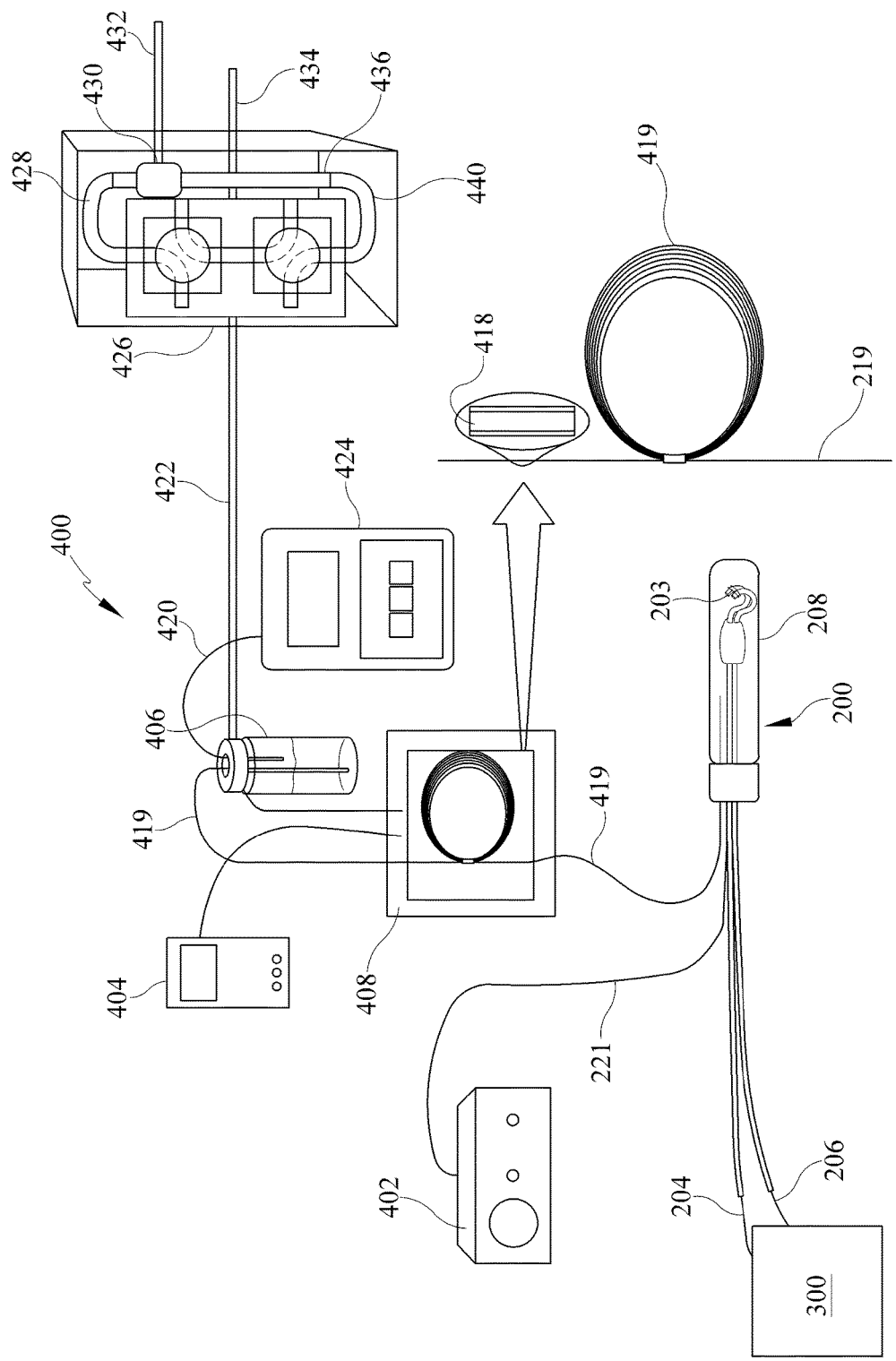
FIG. 7 shows the headspace sampling device of the present disclosure as a component part of a pyro-PLOT-cryo analysis system.

FIG. 7 shows analytical system 400 comprising headspace sampling device 200 configured and disposed to provide a headspace sample to a cryo-PLOT device. Headspace sampling device 200 may be configured and disposed to provide an in situ pyrolysis platform (that is, a pyrolysis platform located inside the headspace collection vial) that provides for rapid heating and rapid vapor capture for a wide variety of samples. In at least one aspect of the present disclosure, headspace sampling device 200 is configured to pyrolize a sample therein and system 400 may be referred to as a pyro-PLOT-cryo system. Headspace sampling device 200 has electrodes 204 and 206 electrically connected to firing circuit 300 at one end and have their other ends disposed in vial 208 and bent to shape a basket 203.

Inlet 221 is in flow communication with electronic pressure controller 402 which is configured to feed a sweep gas into headspace sampling device 200. Outlet 419 may be in flow communication with a lower portion of breakthrough vial 406, having a solvent. Outlet 419 may comprise a PLOT capillary which may have a coil 419 disposed in cryostat 408. Outlet 419 may have a coating 418 on an inner surface thereof. Flow meter 424 may receive the flow gas from outlet 419, after having bubbled through the solvent in the optional breakthrough vial 406.

Cryostat 408 may be configured to cool headspace gas flowing through coil 419. The temperature of cryostat 408 may be controlled with heat transfer line 422. Heat may be transferred to or from cryostat 408 through heat transfer line 422 with two position switching valve 426. Switching valve 426 may be in flow communication with vortex generator 430, compressed air service 432, vent 434, and vortex tube 436. In this configuration, cold may be supplied to two way valve 426 via line 428 and heat may be supplied to two way valve 426 via line 440.

Cryostat 408 may be maintained at a low temperature with vortex tube 430, a device that operates from a source of compressed air 432 and has no moving parts. This aspect may make this approach suitable for environments with explosive or flammable materials. The same vortex tube that is used to generate the low temperature air stream 428 (which can be as low as −40° C.) may also be used to generate a high temperature stream of air 440 (which can be as high as 160° C.) to thermally desorb solutes from the PLOT capillary 419 (or to assist the solvent desorption with more gentle heating). The capillaries that are used may be robust and inexpensive, and unlike other headspace collection methods, pyro-PLOT-cryo may be especially applicable for relatively involatile solutes because it may have a large temperature operability range. Moreover, it may not be limited to aqueous samples, as are some commercial headspace instruments.

EXAMPLES

Objects and uses of this invention may be further illustrated by the following examples, but the particular materials and amounts thereof recited in these examples, as well as other conditions, such as temperatures, and details, should not be construed to unduly limit this invention.

The following examples may provide for a headspace sampling device and method of use. Pyro-PLOT-cryo system 400, shown in FIG. 7, was used for the following examples. After the assembled platform is loaded with sample, and the PLOT-Cryo capillary and helium transfer lines are in place, helium flow is established with a bellows, soap film, or anemometer flow meter. Typical flow rates are between 3 and 8 mL per min. A first set of examples demonstrate enhanced vapor production for analysis of plastic explosives. Plastic explosives form a class of samples that are generally soft solids or semi-solids. The following examples show several examples of analyses in which the sample preparation was done by pyro-PLOT-cryo as shown in FIG. 7.

Example 1

The first sample we present is tagged C4, which was white to grey in color, soft, pliable and sticky. An aliquot of 0.2 mg was loaded onto the pyro-PLOT-cryo platform with a dental string packer. The PLOT capillary (in this and all subsequent examples, aluminum oxide was the adsorbent phase) was placed into the vial, and chilled to 5° C. with the vortex tube. The sample itself was maintained at ambient temperature.

Figure 8A:
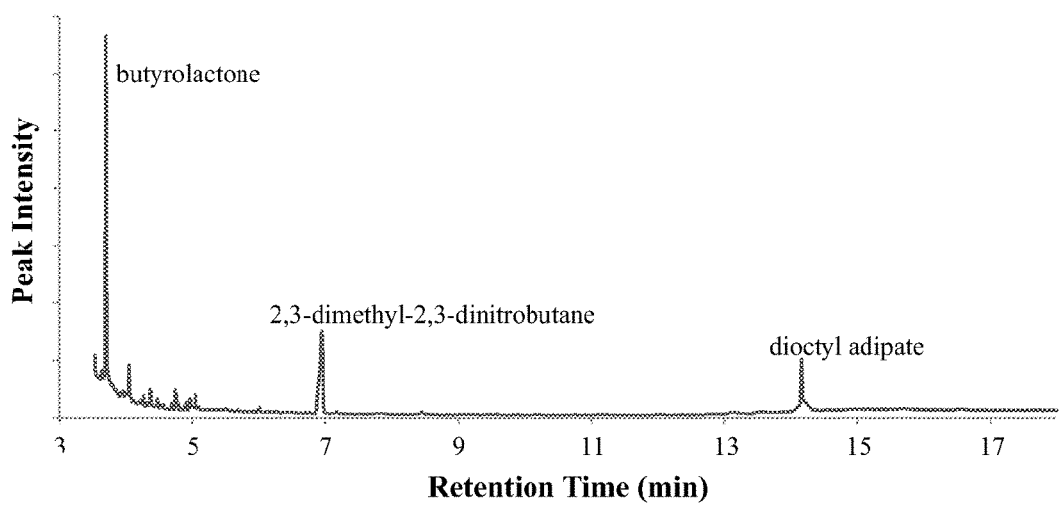
FIG. 8a shows a Chromatogram obtained by GC-MS for vapor collected by use of the pyro-PLOT-cryo shown in FIG. 7 for tagged C4.

Upon discharging the capacitor, the sample was vaporized in a few microseconds, forming a visible cloud in the automatic sampler vial. Vapor was collected for 30 s. The chromatogram shown in FIG. 8a was obtained by analysis by GC-MS after elution of the PLOT capillary with acetone, a solvent chosen because of the moderate polarity. The solution was analyzed by gas chromatography (30 m capillary column of 5% phenyl-95%-dimethyl polysiloxane having a thickness of 1 µm, temperature program from 150 to 225° C., 7° C. per minute) with mass spectrometric detection in scan mode from 20 to 550 RMM units. The taggent (2,3-dimethyl-2,3-dinitrobutane), residual crystallization solvent (butyrolactone) and the plasticizer (dioctyladipate) may easily be identified and quantified by gas chromatography mass spectrometry performed on the resulting solution. The energetic material component, RDX (cyclotrimethylenetrinitramine) was consumed in the pyrolysis and the reaction products were recovered as carbon dioxide, nitrogen and water.

Example 2

Figure 8B:
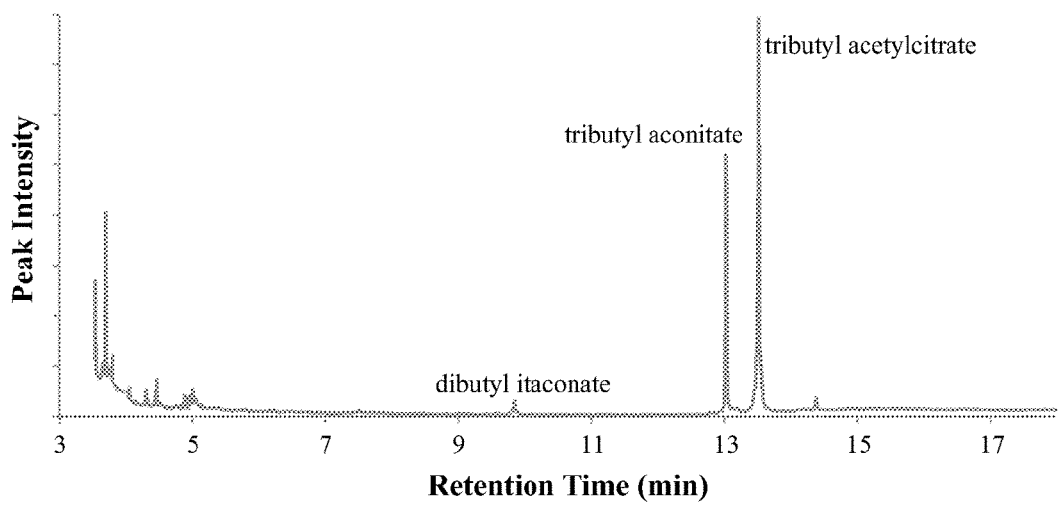
FIG. 8b shows a Chromatogram obtained by GC-MS for vapor collected by use of the pyro-PLOT-cryo shown in FIG. 7 for Deta Flex.

The second sample we present is Deta Flex, a military variant of the industrial cutting compound Detasheet, similar to a plastic explosive although it is often considered a rubberized explosive. The sample was an olive green monolith (6.25 mm thick). As with the C4, a 0.2 mg aliquot (cut from the monolith with a scalpel) was placed in the pyrolysis platform and vaporized, with the resulting products being collected in 30 s by pyro-PLOT-cryo. The chromatogram shown in FIG. 8b was obtained by analysis by GC-MS after elution of the PLOT capillary with acetone. The solution was analyzed by gas chromatography (30 m capillary column of 5% phenyl-95%-dimethyl polysiloxane having a thickness of 1 µm, temperature program from 150 to 225° C., 7° C. per minute) with mass spectrometric detection in scan mode from 20 to 550 RMM units.

We note the presence of three major peaks, all of them plasticizers: dibutyl itaconate (dibutyl 2-methylenesuccinate), tributyl aconitate (1-propene-1,2,3-tricarboxylic acid tributyl ester), and tributyl acetylcitrate (1,2,3-propanetricarboxylic acid, 2-(acetyloxy)-, tributyl ester). There is no taggent or residual solvent visible on the chromatogram. The energetic material, pentaerythritol tetranitrate (PETN), is not present, being pyrolyzed into reaction products as with the RDX above. This chromatogram is significant in that while there is no taggent, the presence of the classical plasticizers used in Deta Flex permits rapid and reliable identification from this small sample.

Example 3

The next sample analyzed with the headspace sampling device of the present disclosure is Semtex H. Semtex H is a plastic explosive containing RDX and PETN. Although it is used in commercial blasting, demolition, and in munitions, it has been extensively used by terrorists because it was, until recently, extremely difficult to detect. It has been recently made more easily detectable by the addition of aluminum powder for x-ray opacity. Detection of vapor remains a difficulty, however. The Semtex H sample we measured was red in color, soft, pliable and sticky. A 0.2 mg aliquot was cut from a monolith with a scalpel, loaded onto the pyrolysis platform by use of a dental string packer, and then vaporized with the PLOT capillary in place. Vapor was collected for 30 s. The chromatogram shown in FIG. 8c was obtained by analysis by GC-MS after elution of the PLOT capillary with acetone. The solution was analyzed by gas chromatography (30 m capillary column of 5% phenyl-95%-dimethyl polysiloxane having a thickness of 1 µm, temperature program from 150 to 225° C., 7° C. per minute) with mass spectrometric detection in scan mode from 20 to 550 RMM units.

Figure 8C:
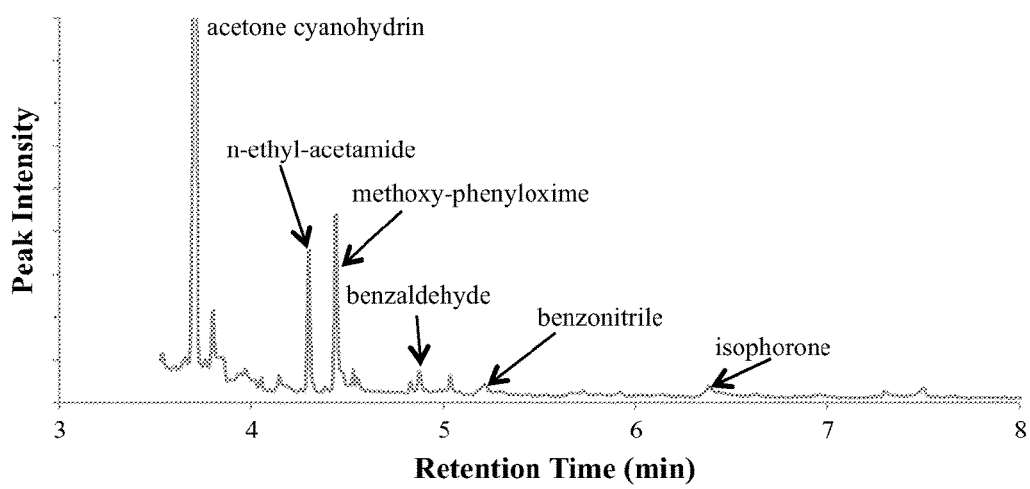
FIG. 8c shows a Chromatogram obtained by GC-MS for vapor collected by use of the pyro-PLOT-cryo shown in FIG. 7 for tagged Semtex H.

As shown in FIG. 8c, a large peak consistent with acetone cyanohydrin (2-hydroxy-2-methyl-propanenitrile), a precursor of the common monomer: methyl methacrylate. It is likely that this compound was formed from the pyrolysis of methyl methacrylate.

Example 4

This example shows enhanced vapor production with a organometallic antiknock additives. For many years, pre-ignition (or pre-detonation) in spark ignition engines was addressed with the addition of the organometallic additive, tetraethyl lead (TEL), to gasoline. Since this additive was phased out in automobile fuel, pre-ignition (and the subsequent engine knock) has been prevented primarily by gasoline formulation with higher concentrations of aromatic compounds, although other organometallic additives are also used for this purpose in some jurisdictions, while being prohibited in other jurisdictions. After-market additives with organometallic components are also used by automotive enthusiasts; again, this is sometimes illegal. An example of an organometallic additive still used is dicyclopentadienyl iron (ferrocene), the classical example of a metallocene "sandwich" compound, consisting of a central iron atom between two cyclopentadienyl rings.

A mixture of gasoline with 37 mg/L ferrocene (the typical additive treatment concentration) was prepared, and the basket of a pyrolysis platform was briefly immersed in this mixture and the gasoline allowed to evaporate, leaving 0.03 mg of residue. This residue contained the ferrocene, which has a relatively high boiling temperature (249° C.). The PLOT capillary was placed into the vial, and chilled to 5° C. with the vortex tube.

Figure 9:
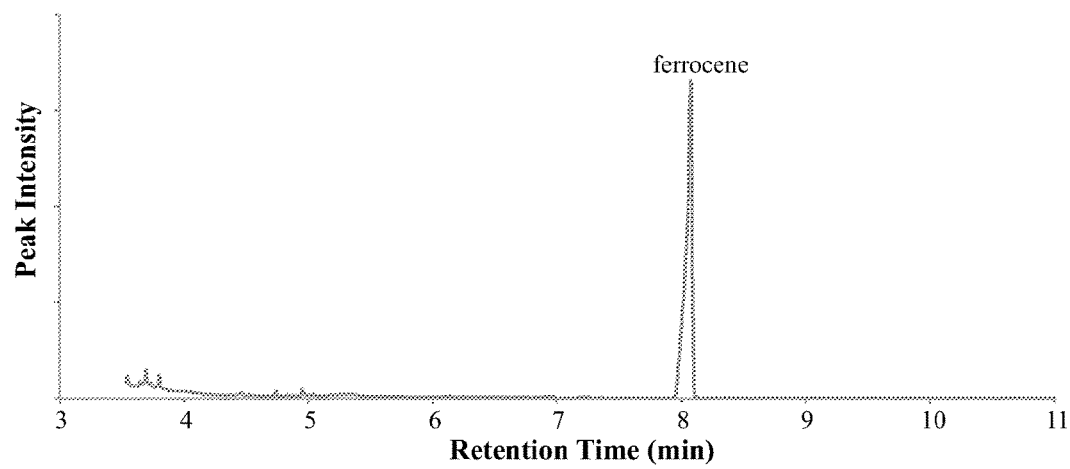
FIG. 9 shows a Chromatogram obtained by GC-MS for vapor collected by use of the pyro-PLOT-cryo shown in FIG. 7 for gasoline with the antiknock additive ferrocene.

Upon discharging the capacitor, the sample was vaporized. Vapor was collected for 30 s. The chromatogram shown in FIG. 9 was obtained by analysis by GC-MS after elution of the PLOT capillary with acetone. The solution was analyzed by gas chromatography (30 m capillary column of 5% phenyl-95%-dimethyl polysiloxane having a thickness of 1 μm, temperature program from 150 to 225° C., 7° C. per minute) with mass spectrometric detection in scan mode from 20 to 550 RMM units.

We note that there are traces of some heavy components remaining from the gasoline (mainly propyl substituted benzenes), then the large ferrocene peak emerges at a retention time of 8 min. Similar results (not shown here) were obtained with gasoline prepared with another organometallic additive, methylcyclopentadienyl manganese tricarbonyl. These analyses may be significant from a forensic standpoint, since the rapid analysis for antiknock additives is important in environmental enforcement.

Example 5

Figure 10A:
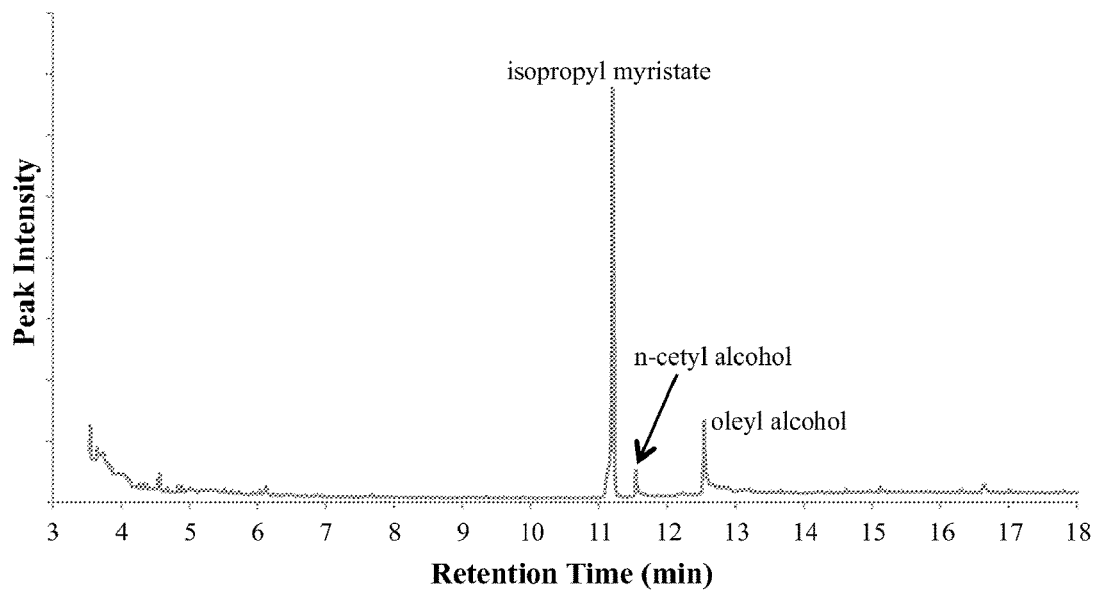
FIG. 10a shows a Chromatogram obtained by GC-MS for vapor collected by use of the pyro-PLOT-cryo shown in FIG. 7 for a typical lip gloss cosmetic.

The analysis of cosmetics may be of great importance in forensic science. As an example of the application of pyro-PLOT-cryo to analyze cosmetics, a small smear (0.06 mg) of red lip gloss was applied to the pyrolysis platform with a dental string packer. The lip gloss is a semisolid, greasy product typically sold in a stick. The PLOT capillary was placed into the vial, and chilled to 5° C. with the vortex tube. Upon discharging the capacitor, the sample was vaporized. Vapor was collected for 30 s. The chromatogram shown in FIG. 10a was obtained by analysis by GC-MS after elution of the PLOT capillary with acetone. The solution was analyzed by gas chromatography (30 m capillary column of 5% phenyl-95%-dimethyl polysiloxane having a thickness of 1 μm, temperature program from 80 to 225° C., 7° C. per minute) with mass spectrometric detection in scan mode from 20 to 550 RMM units.

Three major peaks are observed. Isopropyl myristate (propan-2-yl tetradecanoate) produced the largest peak; it is commonly used in cosmetic and topical medicinal preparations. A small peak consistent with n-cetyl alcohol (1-hexadecanol or palmityl alcohol) is next observed. This compound is used as an emollient, emulsifier or thickener. It is also used as a lubricant in the assembly of threaded fasteners, however, so the presence of this compound alone is not definitive. A third peak, that of oleyl alcohol ((Z)-octadec-9-en-1-ol), combined with the previous two peaks, clearly identifies the product as a cosmetic. This material is used as a nonionic surfactant, emulsifier, emollient and thickener in many skin creams and facial cosmetics.

Example 6

Figure 10B:
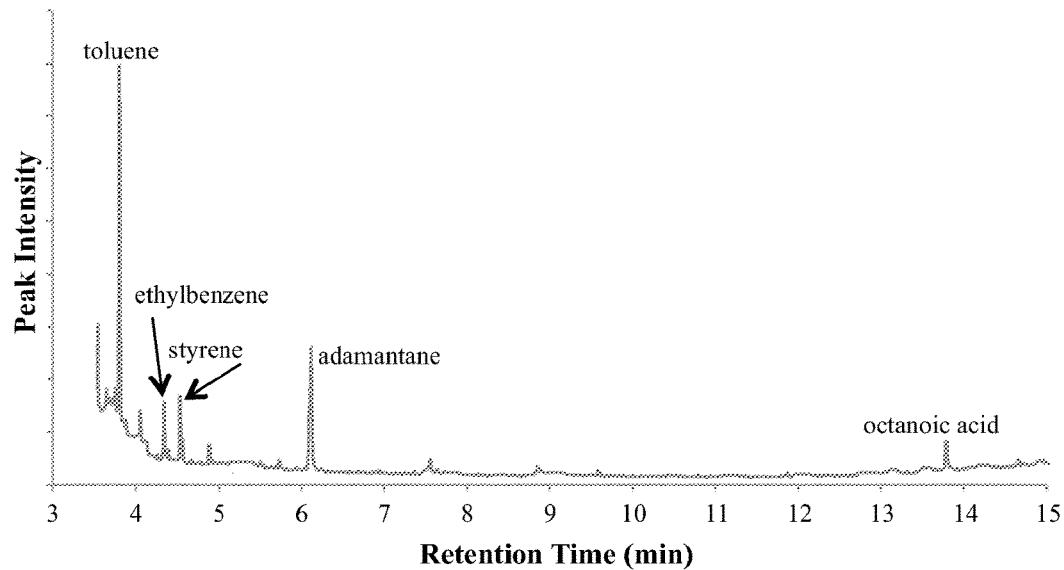
FIG. 10b shows a Chromatogram obtained by GC-MS for vapor collected by use of the pyro-PLOT-cryo shown in FIG. 7 for a typical facial blush cosmetic.

Another somewhat different cosmetic is facial blush, which is analyzed in this example. It is more solid than the lip gloss, exhibiting a more powdery consistency, and is prepared with a polymeric binder. A 0.1 mg chunk of this product was applied to the pyrolysis platform with a dental string packer, and upon discharging the capacitor, the sample was vaporized. The chromatogram shown in FIG. 10b was obtained by analysis by GC-MS after elution of the PLOT capillary with acetone.

In this example, we observe styrene, ethyl benzene and toluene; as we will show later, these compounds are the major pyrolysis products of polystyrene. It was surprising to find adamantane in the vapor as well. While this may be an artifact, adamantane is in fact sometimes used in cosmetics. These analyses may be significant in that forensic determinations of cosmetics are a significant problem requiring rapid methods with simple sample preparations.

Example 7

Figure 11:
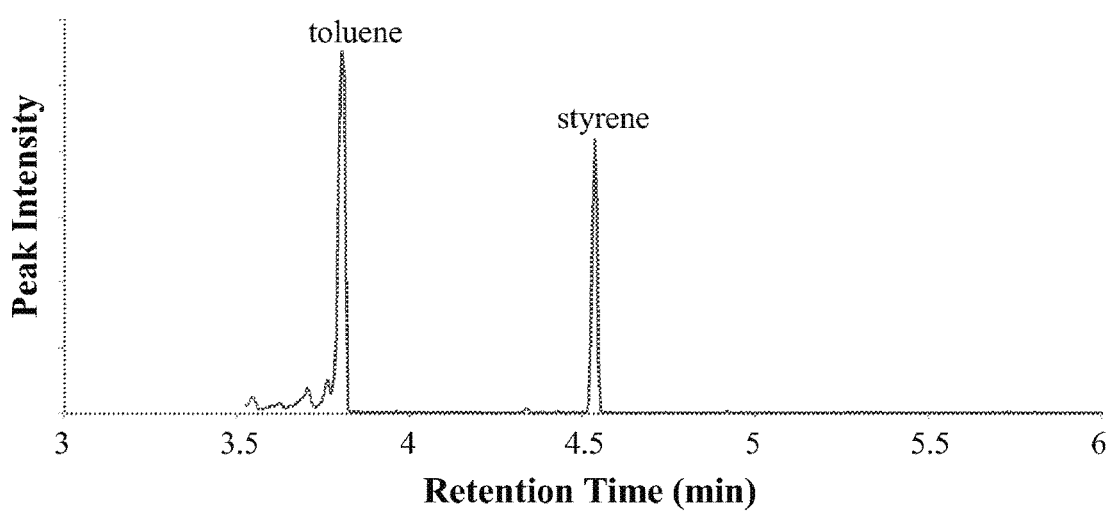
FIG. 11 shows a Chromatogram obtained by GC-MS for vapor collected by use of the pyro-PLOT-cryo shown in FIG. 7 for a sample of polystyrene prepared from a toluene solution.

In this example we show cryo-PLOT-Pyro analysis of polystyrene. While headspace analysis may not ordinarily be applied to a polymer such as polystyrene because of its low vapor pressure, pyrolysis analyses for such polymers have long been routine techniques. We show here that the combination of headspace analysis and pyrolysis can be a very useful approach. The major pyrolysis products of polystyrene, toluene and styrene, are well known. As a demonstration, we have applied two separate sample preparation methods for subsequent product collection by pyro-PLOT-cryo. First, a solution was prepared by dissolving a bead of polystyrene in 1 mL of toluene. The pyrolysis basket was then dipped into this solution, as was done with the gasoline mixtures. The solvent was evaporated in an oven, and a 0.05 mg aliquot of solute polystyrene remained on the basket. The PLOT capillary was placed into the vial, and chilled to 5° C. with the vortex tube. Upon discharging the capacitor, the sample was vaporized. Vapor was collected for 30 s. The chromatogram shown in FIG. 11 was obtained by analysis by GC-MS after elution of the PLOT capillary with acetone.

The solution was analyzed by gas chromatography (30 m capillary column of 5% phenyl-95%-dimethyl polysiloxane having a thickness of 1 μm, temperature program from 80 to 225° C., 7° C. per minute) with mass spectrometric detection in scan mode from 20 to 550 RMM units. The expected pyrolysis products, toluene and styrene, are observed.

To illustrate an alternative sample preparation for polystyrene, a sample was prepared by packing small slivers of a polystyrene packing peanut into a 1.5 mm dental amalgam carrier. The carrier was then compressed to produce a disk that was 1.5 mm in diameter, 0.2 mm thick, with a mass of 0.2 mg. This disk was inserted into the pyrolysis basket with forceps. As before, the PLOT capillary was placed into the vial, and chilled to 5° C. with the vortex tube. Upon discharging the capacitor, the sample was vaporized. Vapor was collected for 30 s, and a chromatogram similar to that of FIG. 11 was obtained by use of the same chromatographic method.

Example 8

In this example, pyrolysis synthesis of cyclopentanone from adipic acid is shown. The pyro-PLOT-cryo approach may be used as a platform for micro scale chemical reactions. The rapid heating produced when the pyrolysis platform is fired can provide the activation energy, and the headspace analysis method can be used to assess reaction products. Such an approach may have application in synthesis reaction evaluation and in academic teaching laboratories.

Figure 12:
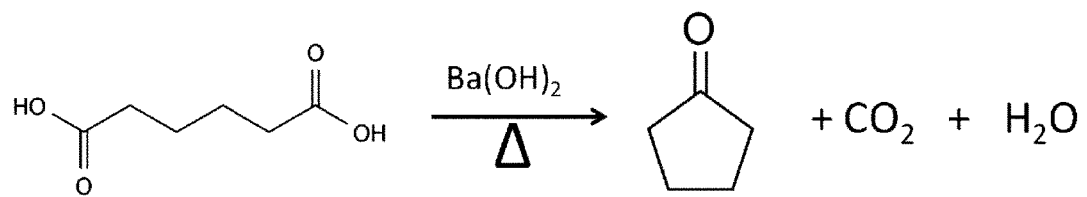
FIG. 12 shows the reaction of five and six carbon cyclic ketones by cyclization and decarboxylation of $\alpha,\zeta$ and $\alpha,\epsilon$-dicarboxylic (1,6- and 1,7-dioic) acids.

In FIG. 12 it is shown that the cyclization reaction that occurs with the pyrolysis of the carboxylate salts of divalent metals results in the formation of a ketone. This may be an especially useful synthesis for five and six carbon cyclic ketones by cyclization and decarboxylation of α,ζ- and α,ε-dicarboxylic (1,6- and 1,7-dioic) acids. The reaction shown in FIG. 12 is that of adipic acid in the presence of the divalent metal base, Ba(OH)2. A typical organic chemistry laboratory manual may describes a typical procedure as follows:

A 21.8 g sample of adipic acid and 1.5 g of Ba(OH)2 were added into a distillation flask that was held in a heating mantle. A condenser and receiver were attached, along with a thermometer rated to 400° C. The flask was heated to approximately 295° C., at which point the solids were melted and the reaction occurred, with the rapid release of carbon dioxide and water, and the condensation of liquid product in the condenser. To carry out the procedure by use of the disclosed invention, the mixture was prepared as a powder in with a mortar and pestle. The pyro-PLOT-cryo was used to supply the energy of activation.

Figure 13:
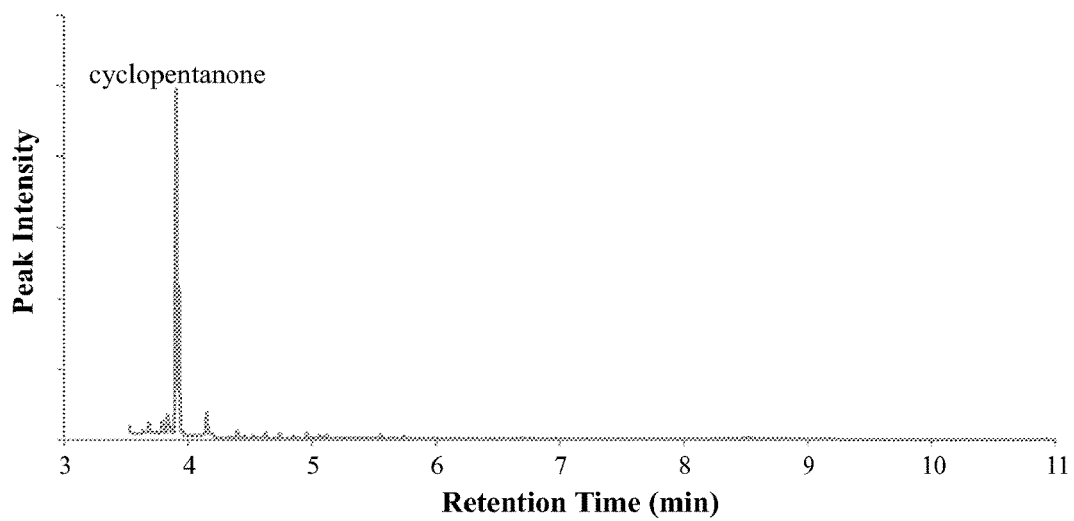
FIG. 13 shows a Chromatogram obtained by GC-MS for vapor collected by use of the pyro-PLOT-cryo shown in FIG. 7 for the reaction mixture of adipic acid barium hydroxide, showing the main product, cyclopentanone.

A 0.2 mg sample of the powdered mixture was placed in the pyrolysis basket, the PLOT capillary was placed into the vial, and chilled to 5° C. with the vortex tube. Upon discharging the capacitor, the reaction was completed essentially instantaneously. Vapor was collected for 30 s, and the chromatogram shown in FIG. 13 was obtained by analysis by GC-MS after elution of the PLOT capillary with acetone.

The solution was analyzed by gas chromatography (30 m capillary column of 5% phenyl-95% dimethyl polysiloxane having a thickness of 1 μm, temperature program from 50 to 100° C., 7° C. per minute) with mass spectrometric detection in scan mode from 20 to 550 RMM units. The main product, cyclopentanone, is clearly shown. This example may illustrate how a relatively tricky and potentially hazardous procedure can be performed very rapidly and safely, with minimal waste, by use of pyro-PLOT-cryo.

The invention claimed is:

1. A headspace sampling device comprising:
  a vial;
  a capacitor firing circuit;
  a sample holding device comprising:
    a first electrode in electrical communication with the capacitor firing circuit;
    a second electrode in electrical communication with the capacitor firing circuit and gap spaced from the first electrode; and
    a basket comprising a continuous strand of wire wrapped around the first electrode and the second electrode and spanning the gap space therebetween;
  the basket being configured to hold and heat a sample therewith and volatize at least a portion of the held sample upon an electrical current being passed through the first electrode, the basket, and the second electrode;
  wherein the wire is pyrolizable upon being rapidly heated with an electrical current being passed through the first electrode, the basket, and the second electrode;
  the sample holding device being configured to seal the basket in the vial; and
  wherein the capacitor firing circuit has a capacity sufficient to pyrolyze the wire upon discharging an electrical current.

2. The headspace sampling device of claim 1 wherein the vial further comprises a gas inlet and a gas outlet.

3. The headspace sampling device of claim 1 wherein the basket comprises at least one of stainless steel, nickel-chromium containing alloys, tungsten, tungsten alloys, platinum, platinum alloys, and other chemically stable materials with a high electrical resistance.

4. The headspace sampling device of claim 1 wherein the wire has a diameter between about 0.0005 inch and 0.0025 inch.

5. The headspace sampling device of claim 1 wherein the basket comprises the at least one continuous strand of wire wrapped around the first electrode and the second electrode a plurality of times and the basket comprises a plurality of spaced lengths of the continuous strand of wire.

6. The headspace sampling device of claim 5 wherein the first electrode and the second electrode are curved and the basket has an approximating half-circle or hook shape.

7. A headspace sampling device comprising:
  a sample basket sealed in a sample container and configured and disposed to hold a liquid, semi-solid, or solid sample;
  a pair of electrodes extending into the sealed container and each having a curved portion configured and disposed to form and hold the sample basket;
  a capacitor firing circuit in electrical communication with the pair of electrodes, the capacitor firing circuit having a capacity sufficient to pyrolyze the basket upon discharging an electrical current;
  the sample basket being pyrolyzable and configured to be rapidly heated and pyrolyzed and to heat a sample held therewith, upon an electrical current being passed through the pair of electrodes with a discharge of the capacitor firing circuit.

8. The headspace sampling device of claim 7 wherein the basket is configured to pyrolyze the sample upon an electrical current being passed through the pair of electrodes.

9. The headspace sampling device of claim 7 wherein the basket comprises wire wound about the pair of electrodes.

10. The headspace sampling device of claim 7 further comprising a gas outlet.

11. The headspace sampling device of claim 10 wherein the gas outlet comprises a porous layer open tubular column.

12. The headspace sampling device of claim 11 wherein the gas outlet passes through a cryostat.

13. The headspace sampling device of claim 7 further comprising a gas inlet.

14. The headspace sampling device of claim 13 further comprising an electronic pressure controller configured and disposed to supply a sweep gas into the gas inlet.

15. A method of headspace sampling comprising the steps of:
  providing a sample basket having an approximating half-circle or hook shape;
  placing a solid, semi-solid, or liquid sample on the sample basket and holding the sample therewith;
  sealing the sample basket holding the sample in a container or vial;
  electrically and rapidly heating the basket and volitizing at least a portion of the sample;
  pyrolyzing the basket upon being rapidly heated; and
  analyzing the volitized portion of the sample.

16. The method of headspace sampling of claim 15 wherein the step of electrically and rapidly heating the basket and volitizing at least a portion of the sample comprises pyrolyzing at least a portion of the sample.

* * * * *